(12) United States Patent
Naranjo-Tackman et al.

(10) Patent No.: US 8,382,745 B2
(45) Date of Patent: Feb. 26, 2013

(54) LASER SYSTEM AND METHOD FOR ASTIGMATIC CORRECTIONS IN ASSOCIATION WITH CATARACT TREATMENT

(75) Inventors: Ramón Naranjo-Tackman, Mexico City (MX); Jorge Octavio Villar Kuri, Mexico City (MX); Rudolph W. Frey, Maitland, FL (US)

(73) Assignee: LensAR, Inc., Orlando, FL (US)

( * ) Notice: Subject to any disclaimer, the term of this patent is extended or adjusted under 35 U.S.C. 154(b) by 252 days.

(21) Appl. No.: 12/831,845

(22) Filed: Jul. 7, 2010

(65) Prior Publication Data

US 2011/0166557 A1 Jul. 7, 2011

Related U.S. Application Data

(60) Provisional application No. 61/228,514, filed on Jul. 24, 2009.

(51) Int. Cl.
*A61B 18/18* (2006.01)
(52) U.S. Cl. .................... 606/5; 606/4; 606/10
(58) Field of Classification Search .............. 606/4, 5, 606/6, 10, 11, 12
See application file for complete search history.

(56) References Cited

U.S. PATENT DOCUMENTS

| | | | |
|---|---|---|---|
| 3,074,407 A | 1/1963 | Moon et al. |
| 3,971,382 A | 7/1976 | Krasnov |
| 3,982,541 A | 9/1976 | L'Esperance, Jr. |
| 4,024,852 A | 5/1977 | L'Esperance et al. |
| 4,263,893 A | 4/1981 | Pavlak et al. |
| 4,309,998 A | 1/1982 | Rosa et al. |
| 4,334,736 A | 6/1982 | Herbert |
| 4,381,007 A | 4/1983 | Doss |
| 4,394,144 A | 7/1983 | Aoki |
| 4,461,294 A | 7/1984 | Baron |
| 4,477,159 A | 10/1984 | Mizuno et al. |
| 4,502,816 A | 3/1985 | Creter, Jr. et al. |
| 4,517,980 A | 5/1985 | Tagnon |
| 4,537,193 A | 8/1985 | Tanner |
| 4,538,608 A | 9/1985 | L'Esperance, Jr. |
| 4,554,917 A | 11/1985 | Tagnon |
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |

(Continued)

FOREIGN PATENT DOCUMENTS

| | | |
|---|---|---|
| CA | 2553963 A1 | 8/2005 |
| CA | 2680072 A1 | 9/2008 |
| EP | 0 397 962 A1 | 11/1990 |
| FR | 2 497 087 A1 | 7/1982 |
| JP | 5-115437 A | 5/1993 |

(Continued)

OTHER PUBLICATIONS

Written Opinion of the International Searching Authority, PCT/ISA/237, prepared for International Application PCT/US2010/041324 on Sep. 23, 2010.*

(Continued)

*Primary Examiner* — David N Spector
(74) *Attorney, Agent, or Firm* — Brinks Hofer Gilson & Lione

(57) ABSTRACT

There is provided a system, apparatus and methods for developing laser systems that can create precise predetermined clear corneal incisions that are capable of reducing astigmatism. The systems, apparatus and methods further provide laser systems that can provide these incisions at or below Bowman's membrane and in conjunction a precise predetermined capsulotomy shot pattern.

25 Claims, 2 Drawing Sheets

U.S. PATENT DOCUMENTS

| | | |
|---|---|---|
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch et al. |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Schroder et al. |
| 4,702,576 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Weinberg |
| 4,721,379 A | 1/1988 | L'Esperance |
| 4,724,522 A | 2/1988 | Belgorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,741,612 A | 5/1988 | Birngruber et al. |
| 4,744,362 A | 5/1988 | Gründler |
| 4,758,081 A | 7/1988 | Barnes |
| 4,765,336 A | 8/1988 | Blaha et al. |
| 4,770,162 A | 9/1988 | L'Esperance et al. |
| 4,770,172 A | 9/1988 | L'Esperance, Jr. |
| 4,770,486 A | 9/1988 | Wang et al. |
| 4,772,116 A | 9/1988 | Schroder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,884,884 A | 12/1989 | Reis |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiyama |
| 4,901,718 A | 2/1990 | Billie et al. |
| 4,902,124 A | 2/1990 | Roy, Sr. et al. |
| 4,903,695 A | 2/1990 | Warner et al. |
| 4,905,711 A | 3/1990 | Bennett et al. |
| 4,907,586 A | 3/1990 | Billie et al. |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance, Jr. |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell, Jr. et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,054,907 A | 10/1991 | Sklar et al. |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,098,426 A | 3/1992 | Sklar et al. |
| 5,102,409 A | 4/1992 | Balgorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance, III et al. |
| 5,152,759 A | 10/1992 | Parel et al. |
| 5,163,934 A | 11/1992 | Munnerlyn |
| 5,171,242 A | 12/1992 | Dewey et al. |
| 5,174,021 A | 12/1992 | L'Esperance, III et al. |
| 5,178,635 A | 1/1993 | Gwon et al. |
| 5,188,631 A | 2/1993 | L'Esperance, Jr. |
| 5,194,948 A | 3/1993 | L'Esperance, III et al. |
| 5,196,006 A | 3/1993 | Klopotek et al. |
| 5,196,027 A | 3/1993 | Thompson et al. |
| 5,201,730 A | 4/1993 | Easley et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Billie et al. |
| 5,246,436 A | 9/1993 | Rowe |
| 5,257,988 A | 11/1993 | L'Esperance, Jr. |
| 5,258,025 A | 11/1993 | Fedorov et al. |
| 5,263,950 A | 11/1993 | L'Esperance, Jr. |
| 5,263,951 A | 11/1993 | Spears et al. |
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |
| 5,282,798 A | 2/1994 | Bruse et al. |
| 5,284,477 A | 2/1994 | Hanna et al. |
| 5,288,293 A | 2/1994 | O'Donnell, Jr. |
| 5,290,272 A | 3/1994 | Burstein et al. |
| 5,295,989 A | 3/1994 | Nakamura |
| 5,300,020 A | 4/1994 | L'Esperance, Jr. |
| 5,300,061 A | 4/1994 | Easley et al. |
| 5,300,062 A | 4/1994 | Ueno |
| 5,300,063 A | 4/1994 | Tano et al. |

| | | | | | | |
|---|---|---|---|---|---|---|
| 5,300,114 A | 4/1994 | Gwon et al. | | 5,616,139 A | 4/1997 | Okamoto |
| 5,304,168 A | 4/1994 | Sun | | 5,618,284 A | 4/1997 | Sand |
| 5,304,169 A | 4/1994 | Sand | | 5,620,435 A | 4/1997 | Belkin et al. |
| 5,311,224 A | 5/1994 | Enomoto | | 5,627,162 A | 5/1997 | Gwon et al. |
| 5,312,320 A | 5/1994 | L'Esperance, Jr. | | 5,632,742 A | 5/1997 | Frey et al. |
| 5,312,393 A | 5/1994 | Mastel | | 5,651,782 A | 7/1997 | Simon et al. |
| 5,314,422 A | 5/1994 | Nizzola | | 5,656,186 A | 8/1997 | Mourou et al. |
| 5,318,047 A | 6/1994 | Davenport et al. | | 5,684,560 A | 11/1997 | Roffman et al. |
| 5,318,560 A | 6/1994 | Blount et al. | | 5,699,142 A | 12/1997 | Lee et al. |
| 5,323,788 A | 6/1994 | Silvestrini et al. | | 5,709,868 A | 1/1998 | Perricone |
| 5,324,281 A | 6/1994 | Muller | | 5,722,952 A | 3/1998 | Schachar |
| 5,325,134 A | 6/1994 | Kohayakawa | | 5,722,970 A | 3/1998 | Colvard et al. |
| 5,334,190 A | 8/1994 | Seiler | | 5,731,909 A | 3/1998 | Schachar |
| 5,336,215 A | 8/1994 | Hsueh et al. | | 5,738,677 A | 4/1998 | Colvard et al. |
| 5,336,216 A | 8/1994 | Dewey | | 5,752,950 A | 5/1998 | Frey et al. |
| 5,342,351 A | 8/1994 | Blaha et al. | | 5,773,472 A | 6/1998 | Stjernschantz et al. |
| 5,342,370 A | 8/1994 | Simon et al. | | 5,828,686 A | 10/1998 | Frey et al. |
| 5,345,948 A | 9/1994 | O'Donnell, Jr. | | 5,843,184 A | 12/1998 | Cionni |
| 5,346,491 A | 9/1994 | Oertli | | 5,849,006 A | 12/1998 | Frey et al. |
| 5,347,329 A | 9/1994 | Ota | | 5,886,768 A | 3/1999 | Knopp et al. |
| 5,348,551 A | 9/1994 | Spears et al. | | 5,907,908 A | 6/1999 | Cunanan et al. |
| 5,350,374 A | 9/1994 | Smith | | 5,912,915 A | 6/1999 | Reed et al. |
| 5,354,331 A | 10/1994 | Schachar | | 5,919,186 A | 7/1999 | Bath |
| 5,355,181 A | 10/1994 | Ashizaki et al. | | 5,980,513 A | 11/1999 | Frey et al. |
| 5,356,407 A | 10/1994 | Easley et al. | | 5,984,916 A | 11/1999 | Lai |
| 5,356,409 A | 10/1994 | Nizzola | | 5,993,441 A | 11/1999 | Muller et al. |
| 5,360,424 A | 11/1994 | Klopotek | | 6,007,578 A | 12/1999 | Schachar |
| 5,364,388 A | 11/1994 | Koziol | | 6,013,101 A | 1/2000 | Israel |
| 5,364,390 A | 11/1994 | Taboada et al. | | 6,019,472 A | 2/2000 | Koester et al. |
| 5,368,590 A | 11/1994 | Itoh | | 6,022,088 A | 2/2000 | Metzler |
| 5,370,641 A | 12/1994 | O'Donnell, Jr. | | 6,027,494 A | 2/2000 | Frey |
| 5,372,595 A | 12/1994 | Gaasterland et al. | | 6,050,687 A | 4/2000 | Billie et al. |
| 5,374,265 A | 12/1994 | Sand | | 6,055,259 A | 4/2000 | Frey et al. |
| 5,376,086 A | 12/1994 | Khoobehi et al. | | 6,059,772 A | 5/2000 | Hsia et al. |
| 5,391,165 A | 2/1995 | Fountain et al. | | 6,070,981 A | 6/2000 | Mihashi et al. |
| 5,395,356 A | 3/1995 | King et al. | | 6,099,522 A | 8/2000 | Knopp et al. |
| 5,403,307 A | 4/1995 | Zelman | | 6,114,651 A | 9/2000 | Schluter et al. |
| 5,408,484 A | 4/1995 | Weimel | | 6,132,424 A | 10/2000 | Tang |
| 5,411,501 A | 5/1995 | Klopotek | | 6,186,148 B1 | 2/2001 | Okada |
| 5,412,561 A | 5/1995 | Rosenshein et al. | | 6,190,375 B1 | 2/2001 | Frey |
| 5,413,555 A | 5/1995 | McMahan | | 6,197,018 B1 | 3/2001 | O'Donnell |
| 5,423,798 A | 6/1995 | Crow | | 6,197,056 B1 | 3/2001 | Schachar |
| 5,423,800 A | 6/1995 | Ren et al. | | 6,252,595 B1 | 6/2001 | Birmingham et al. |
| 5,423,801 A | 6/1995 | Marshall et al. | | 6,254,595 B1 | 7/2001 | Juhasz et al. |
| 5,425,727 A | 6/1995 | Koziol | | 6,261,220 B1 | 7/2001 | Frey et al. |
| 5,425,729 A | 6/1995 | Ishida et al. | | 6,271,914 B1 | 8/2001 | Frey et al. |
| 5,425,730 A | 6/1995 | Luloh | | 6,271,915 B1 | 8/2001 | Frey et al. |
| 5,437,657 A | 8/1995 | Epstein | | 6,275,718 B1 | 8/2001 | Lempert |
| 5,437,658 A | 8/1995 | Muller et al. | | 6,280,435 B1 | 8/2001 | Odrich et al. |
| 5,439,462 A | 8/1995 | Bille et al. | | 6,280,468 B1 | 8/2001 | Schachar |
| 5,441,496 A | 8/1995 | Easley et al. | | 6,299,640 B1 | 10/2001 | Schachar |
| 5,441,511 A | 8/1995 | Hanna | | 6,302,879 B1 | 10/2001 | Frey et al. |
| 5,442,412 A | 8/1995 | Frey et al. | | 6,312,422 B1 | 11/2001 | Duback |
| 5,442,487 A | 8/1995 | Mizuno | | 6,312,424 B1 | 11/2001 | Largent |
| 5,445,633 A | 8/1995 | Nakamura et al. | | 6,313,165 B1 | 11/2001 | Grunberger et al. |
| 5,460,627 A | 10/1995 | O'Donnell, Jr. | | 6,315,773 B1 | 11/2001 | Frey et al. |
| 5,461,212 A | 10/1995 | Seiler et al. | | 6,319,274 B1 | 11/2001 | Shadduck |
| 5,462,739 A | 10/1995 | Dan et al. | | 6,322,545 B1 | 11/2001 | Schachar |
| 5,465,737 A | 11/1995 | Schachar | | 6,322,556 B1 | 11/2001 | Gwon et al. |
| 5,470,329 A | 11/1995 | Sumiya | | 6,324,191 B1 | 11/2001 | Horvath |
| 5,474,548 A | 12/1995 | Knopp et al. | | 6,325,791 B1 | 12/2001 | Shimoji |
| 5,476,511 A | 12/1995 | Gwon et al. | | 6,325,792 B1 * | 12/2001 | Swinger et al. ............ 606/4 |
| 5,480,396 A | 1/1996 | Simon et al. | | 6,328,732 B1 | 12/2001 | Donitzky et al. |
| 5,484,432 A | 1/1996 | Sand | | 6,344,040 B1 | 2/2002 | Juhasz et al. |
| 5,489,299 A | 2/1996 | Schachar | | 6,373,571 B1 | 4/2002 | Juhasz et al. |
| 5,503,165 A | 4/1996 | Schachar | | D459,806 S | 7/2002 | Webb |
| 5,507,740 A | 4/1996 | O'Donnell, Jr. | | D459,807 S | 7/2002 | Webb |
| 5,514,124 A | 5/1996 | Alpins | | 6,413,262 B2 | 7/2002 | Saishin et al. |
| 5,514,125 A | 5/1996 | Lasser et al. | | D462,442 S | 9/2002 | Webb |
| 5,520,679 A | 5/1996 | Lin | | D462,443 S | 9/2002 | Webb |
| 5,527,774 A | 6/1996 | Girard | | 6,451,008 B1 | 9/2002 | Frey et al. |
| 5,529,076 A | 6/1996 | Schachar | | 6,460,997 B1 | 10/2002 | Frey et al. |
| 5,533,997 A | 7/1996 | Ruiz | | 6,467,906 B1 | 10/2002 | Alpins |
| 5,548,352 A | 8/1996 | Dewey | | 6,493,151 B2 | 12/2002 | Schachar |
| 5,549,597 A | 8/1996 | Shimmick et al. | | 6,494,910 B1 | 12/2002 | Ganem et al. |
| 5,556,395 A | 9/1996 | Shimmick et al. | | 6,497,483 B2 | 12/2002 | Frey et al. |
| 5,573,544 A | 11/1996 | Simon et al. | | 6,530,917 B1 | 3/2003 | Seiler et al. |
| 5,594,753 A | 1/1997 | Frey et al. | | 6,544,254 B1 | 4/2003 | Bath |
| 5,607,472 A | 3/1997 | Thompson | | 6,547,394 B2 | 4/2003 | Doherty |

| | | |
|---|---|---|
| 6,554,825 B1 | 4/2003 | Murray et al. |
| 6,585,726 B2 | 7/2003 | Frey et al. |
| 6,588,902 B2 | 7/2003 | Isogai |
| 6,610,686 B1 | 8/2003 | Enrico et al. |
| 6,623,476 B2 | 9/2003 | Juhasz et al. |
| 6,626,445 B2 | 9/2003 | Murphy et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Lieberman et al. |
| 6,676,653 B2 | 1/2004 | Juhasz et al. |
| 6,693,927 B1 | 2/2004 | Horvath et al. |
| 6,702,853 B1 | 3/2004 | Peyman |
| 6,726,679 B1 | 4/2004 | Dick et al. |
| 6,849,091 B1 | 2/2005 | Cumming |
| 6,863,667 B2 | 3/2005 | Webb et al. |
| 6,905,641 B2 | 6/2005 | Platt et al. |
| 6,923,955 B2 | 8/2005 | Till et al. |
| 6,962,583 B2 | 11/2005 | Kadziauskas et al. |
| 7,044,568 B2 | 5/2006 | Olivera et al. |
| 7,077,838 B2 | 7/2006 | Wong |
| 7,182,759 B2 | 2/2007 | Kadziauskas et al. |
| 7,188,949 B2 | 3/2007 | Bandhauer et al. |
| 7,220,255 B2 | 5/2007 | Lai |
| 7,252,662 B2 | 8/2007 | McArdle et al. |
| RE40,002 E | 1/2008 | Lin |
| RE40,184 E | 3/2008 | Lin |
| 7,338,167 B2 | 3/2008 | Zelvin et al. |
| 7,357,504 B2 | 4/2008 | Fischer et al. |
| 7,364,575 B2 | 4/2008 | Van Saarloos |
| 7,390,089 B2 | 6/2008 | Loesel et al. |
| RE40,420 E | 7/2008 | Dick et al. |
| 7,402,159 B2 | 7/2008 | Loesel et al. |
| 7,467,871 B2 | 12/2008 | Lawhorn et al. |
| 7,540,613 B2 | 6/2009 | Severns |
| 7,655,002 B2 | 2/2010 | Myers |
| 7,717,908 B2 | 5/2010 | Ruiz et al. |
| 7,766,903 B2 | 8/2010 | Blumenkranz et al. |
| 7,836,894 B2 | 11/2010 | Brinkmann et al. |
| 8,262,553 B2 | 9/2012 | Weston et al. |
| 8,262,646 B2 | 9/2012 | Frey et al. |
| 2001/0029363 A1 | 10/2001 | Lin |
| 2002/0004658 A1 | 1/2002 | Munnerlyn et al. |
| 2002/0025311 A1 | 2/2002 | Till |
| 2002/0029053 A1 | 3/2002 | Gordon |
| 2002/0049450 A1 | 4/2002 | Myers |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2002/0159028 A1 | 10/2002 | Masaki |
| 2003/0050629 A1 | 3/2003 | Kadziauskas et al. |
| 2003/0055412 A1 | 3/2003 | Lieberman et al. |
| 2003/0076477 A1 | 4/2003 | Matsumoto |
| 2003/0109926 A1 | 6/2003 | Portney |
| 2003/0135272 A1 | 7/2003 | Brady et al. |
| 2003/0139737 A1 | 7/2003 | Lin |
| 2003/0212387 A1 | 11/2003 | Kurtz et al. |
| 2003/0220630 A1 | 11/2003 | Lin et al. |
| 2004/0054359 A1 | 3/2004 | Ruiz et al. |
| 2004/0059321 A1 | 3/2004 | Knopp et al. |
| 2004/0070761 A1 | 4/2004 | Horvath et al. |
| 2004/0143244 A1 | 7/2004 | Gray et al. |
| 2004/0156014 A1 | 8/2004 | Piers et al. |
| 2004/0199149 A1 | 10/2004 | Myers et al. |
| 2004/0199150 A1 | 10/2004 | Lai |
| 2004/0243111 A1 | 12/2004 | Bendett et al. |
| 2004/0249403 A1 | 12/2004 | Loomas et al. |
| 2005/0107773 A1 | 5/2005 | Bergt et al. |
| 2005/0107775 A1 | 5/2005 | Huang et al. |
| 2005/0165387 A1 | 7/2005 | Lubatschowski et al. |
| 2005/0197655 A1 | 9/2005 | Telfair et al. |
| 2005/0203492 A1 | 9/2005 | Nguyen et al. |
| 2005/0243276 A1 | 11/2005 | Van Heugten et al. |
| 2006/0058682 A1 | 3/2006 | Miller et al. |

| | | | |
|---|---|---|---|
| 2006/0192921 A1 | 8/2006 | Loesel et al. | |
| 2006/0195076 A1 | 8/2006 | Blumenkranz et al. | |
| 2006/0215111 A1 | 9/2006 | Mihashi | |
| 2006/0259022 A1 | 11/2006 | Lin | |
| 2007/0078447 A1 | 4/2007 | Weinacht et al. | |
| 2007/0084694 A1 | 4/2007 | Doherty et al. | |
| 2007/0093795 A1 | 4/2007 | Melcher et al. | |
| 2007/0093796 A1 | 4/2007 | Raksi et al. | |
| 2007/0129693 A1 | 6/2007 | Hunter et al. | |
| 2007/0173794 A1 | 7/2007 | Frey et al. | |
| 2007/0173795 A1 | 7/2007 | Frey et al. | |
| 2007/0185475 A1 | 8/2007 | Frey et al. | |
| 2007/0265603 A1 | 11/2007 | Pinelli | |
| 2008/0071254 A1 | 3/2008 | Lummis et al. | |
| 2008/0111972 A1 | 5/2008 | Barth et al. | |
| 2008/0114386 A1 | 5/2008 | Iliakis et al. | |
| 2008/0186551 A1 | 8/2008 | Hanft et al. | |
| 2008/0281303 A1 | 11/2008 | Culbertson et al. | |
| 2008/0281413 A1 | 11/2008 | Culbertson et al. | |
| 2008/0312675 A1 | 12/2008 | Newcott et al. | |
| 2009/0069794 A1 | 3/2009 | Kurtz | |
| 2009/0088734 A1 | 4/2009 | Mordaunt | |
| 2009/0126870 A1 | 5/2009 | Zadoyan et al. | |
| 2009/0131921 A1 | 5/2009 | Kurtz | |
| 2009/0137988 A1 | 5/2009 | Kurtz | |
| 2009/0137991 A1 | 5/2009 | Kurtz | |
| 2009/0137993 A1 * | 5/2009 | Kurtz | 606/6 |
| 2009/0157063 A1 * | 6/2009 | Ruiz et al. | 606/5 |
| 2009/0161065 A1 | 6/2009 | Smith, III et al. | |
| 2009/0171327 A1 | 7/2009 | Kurtz et al. | |
| 2009/0177189 A1 | 7/2009 | Raksi | |
| 2009/0244482 A1 | 10/2009 | Eisener et al. | |
| 2009/0281530 A1 | 11/2009 | Korn | |
| 2010/0002837 A1 | 1/2010 | Gertner et al. | |
| 2010/0004641 A1 | 1/2010 | Frey et al. | |
| 2010/0004643 A1 | 1/2010 | Frey et al. | |
| 2010/0022994 A1 | 1/2010 | Frey et al. | |
| 2010/0022995 A1 | 1/2010 | Frey et al. | |
| 2010/0022996 A1 | 1/2010 | Frey et al. | |
| 2010/0042079 A1 | 2/2010 | Frey et al. | |
| 2010/0060855 A1 | 3/2010 | Graether | |
| 2010/0114079 A1 | 5/2010 | Myers et al. | |
| 2010/0256614 A1 | 10/2010 | Donitzky et al. | |
| 2010/0256615 A1 | 10/2010 | Blumenkranz et al. | |
| 2010/0274228 A1 | 10/2010 | Mrochen et al. | |
| 2010/0292676 A1 | 11/2010 | Larsen | |
| 2010/0292678 A1 | 11/2010 | Frey et al. | |
| 2010/0312231 A1 | 12/2010 | Singh | |
| 2010/0324542 A1 | 12/2010 | Kurtz | |
| 2010/0331829 A1 | 12/2010 | Bor et al. | |
| 2011/0022035 A1 | 1/2011 | Porter et al. | |
| 2011/0022036 A1 | 1/2011 | Frey et al. | |
| 2011/0028950 A1 | 2/2011 | Raksi et al. | |
| 2011/0092965 A1 | 4/2011 | Slatkine | |
| 2011/0118712 A1 | 5/2011 | Lubatschowski et al. | |
| 2011/0137301 A1 | 6/2011 | Bartoli | |
| 2011/0149240 A1 | 6/2011 | Alpins | |
| 2011/0160710 A1 | 6/2011 | Frey et al. | |
| 2011/0160711 A1 | 6/2011 | Naranjo-Tackman et al. | |
| 2011/0184395 A1 | 7/2011 | Schuele et al. | |
| 2011/0187995 A1 | 8/2011 | Frey et al. | |
| 2011/0190739 A1 | 8/2011 | Frey et al. | |
| 2011/0190740 A1 | 8/2011 | Frey et al. | |
| 2011/0292340 A1 | 12/2011 | Shimizu et al. | |
| 2012/0182522 A1 | 7/2012 | Frey et al. | |

FOREIGN PATENT DOCUMENTS

| | | |
|---|---|---|
| WO | WO 91/19539 A1 | 12/1991 |
| WO | WO 01/13838 A1 | 3/2001 |
| WO | WO 2005/070358 A1 | 8/2005 |
| WO | WO 2011011205 A1 * | 1/2011 |
| WO | WO 2012/051490 A1 | 4/2012 |

OTHER PUBLICATIONS

FDA PMA P030002 titled "crystalens™ Model AT-45 Accomodating Posterior Chamber Intraocular Lens (OIO)", dated Nov. 14, 2003, 16 pgs.

FDA PMA P040020 titled "AcrySof® ResSTOR® Apodized Diffractive Optic Posterior Chamber Intraocular Lenses, Models MA60d3 and SA60D3", dated Mar. 21, 2005, 29 pgs.
International Preliminary Report on Patentability for App. No. PCT/US2011/022859, dated Aug. 9, 2012, 9 pgs.
International Preliminary Report on Patentability for App. No. PCT/US2011/023117, dated Aug. 16, 2012, 6 pgs.
International Preliminary Report on Patentability for App. No. PCT/US2011/023159, dated Aug. 16, 2012, 6 pgs.
Australian Examiner's Report for App. No. 2010274169, dated Aug. 30, 2012, 4 pgs.
International Search Report and Written Opinion for App. No. PCT/US2012/031377, dated Sep. 13, 2012, 17 pgs.
Non-Final Office Action for U.S. Appl. No. 13/017,702, dated Sep. 13, 2012, 8 pgs.
Non-Final Office Action for U.S. Appl. No. 29/377,054, dated Sep. 18, 2012, 7 pgs.
Non-Final Office Action for U.S. Appl. No. 12/685,850, dated Sep. 18, 2012, 9 pgs.
Non-Final Office Action for U.S. Appl. No. 12/831,783, dated Sep. 19, 2012, 9 pgs.
Non-Final Office Action for U.S. Appl. No. 13/017,499, dated Oct. 5, 2012, 38 pgs.
International Search Report for related application No. PCT/US2011/56279, dated Feb. 1, 2012, 9 pgs.
International Search Report and Written Opinion for related application No. PCT/US2012/030247, dated Jul. 9, 2012, 6 pgs.
International Search Report and Written Opinion for related application No. PCT/US2012/030059, dated Jul. 13, 2012, 12 pgs.
International Search Report and Written Opinion for related application No. PCT/US2012/030259, dated Jul. 13, 2012, 11 pgs.
U.S. Appl. No. 13/427,130, filed Mar. 22, 2012 (34 pgs).
U.S. Appl. No. 13/427,149, filed Mar. 22, 2012 (29 pgs).
U.S. Appl. No. 13/427,319, filed Mar. 22, 2012 (32 pgs).
U.S. Appl. No. 13/435,103, filed Mar. 30, 2012 (72 pgs).
Chinese Office Action for related application No. CN 200780009762.6, dated Mar. 2, 2011, 10 pgs.
Chinese Office Action for related application No. CN 200780009762.6, dated Sep, 9, 2010, 9 pgs.
International Search Report dated Sep. 25, 2007 from related PCT application No. PCT/US07/01262, 1 page.
International Search Report dated Oct. 4, 2007 from related PCT application No. PCT/US07/01486, 1 page.
International Search Report dated Oct, 23, 2007 from related PCT application No. PCT/US07/01312, 1 page.
International Search Report dated Jan. 2, 2008 from related PCT application No. PCT/US07/01353, 1 page.
International Search Report and Written Opinion for related application No. PCT/US2011/023159, dated Mar. 16, 2011, 6 pgs.
International Search Report and Written Opinion for related application No. PCT/US2011/023117, dated Mar. 25, 2011, 10 pgs.
International Search Report and Written Opinion for related application No. PCT/US2011/22859, dated Apr. 4, 2011, 7 pgs.
International Search Report and Written Opinion for related application No. PCT/US2010/041286, dated Sep. 14, 2010, 8 pgs.
International Search Report and Written Opinion for related application No. PCT/US2010/042582, dated Sep. 20, 2010, 10 pgs.
International Search Report and Written Opinion for related application No. PCT/US2010/043255, dated Sep. 16, 2010, 10 pgs.
International Search Report for related application No. PCT/US2011/56279, dated Feb. 1, 2012, 2 pgs.
International Search Report and Written Opinion for related application No. PCT/US2010/043117, dated Sep. 10, 2010, 14 pgs.
Author unknown, "Statement of the Use of Animals in Opthalmic and Visual Research", The Association for Research in Vision and Opthalmology, Obtained from the Internet at: http//www.arvo.org/aboutavro as of Nov. 18, 2010, 3 pgs.
Akchurin, Garif et al., "Evaluation of the degree of turbidity if cataract lens and its correlation with retinal visual acuity", *SPIE*, vol. 3591, Jan. 1999, pp. 74-81.
Al-Ghoul, K. J. et al., "Distribution and Type of Morphological Damage in Human Nuclear Age-Related Cataracts", *Department of Cell Biology and Anatomy*, University of North Carolina and Duke University Eye Center, 1996, pp. 237-251.
Al-Ghoul, Kristin J. et al., "Structural Evidence of Human Nuclear Fiber Compaction as a Function of Ageing and Cataractogenesis", *Exp. Eye Res.*, vol. 72, 2001, pp. 199-214.
Alio, et al., "Crystalline Lens Optical Dysfunction through Aging", *Ophthalmology*, vol. 112, No. 11, Nov. 2005, pp. 2022-2029.
Amann, Josef et al., "Increased Endothelial Cell Density in the Paracentral and Peripheral Regions of the Human Cornea", *American Journal of Ophthalmology*, vol. 135, No. 5, May 2003, pp. 584-590.
Amendt, M. Strauss et al., "Modeling of bubble dynamics in relation to medical applications", *Proc. of SPIE*, vol. 2975, 1997, pp. 362-373.
Ansarl, Rafat R. et al., "Measuring lens opacity: combining quasi-elastic light scattering with Scheimpflug imaging system", *Proc. of SPIE*, vol. 3246, 1998, pp. 35-42.
Anschutz, Till, M.D., "Laser Correction of Hyperopia and Presbyopia". vol. 34, No. 4, 1994, pp. 107-137.
Apple, David J. et al., "Preparation and Study of Human Eyes Obtained Postmortem with the Miyake Posterior Photographic Technique", *Ophthalmology*, vol. 97, No. 6, Jun. 1990, pp. 810-816.
Armstrong, Larry "A cataract Breakthrough May Be On The Way", *Business Week*, Mar. 23, 1998, pp. 90-92.
Aston, Adam, "Why Settle for 20/20?", *Business Week*, Mar. 17, 2003, pp. 95-96.
Azzam, Naiel et al., "Long-term lens organ culture system to determine age-related effects of UV irradiation on the eye lens", *Experimental Eye Research*, vol. 79, 2004, pp. 903-911.
Back, Arthur P. et al., "Correction of Presbyopia with Contact Lenses: Comparative Success Rates with Three Systems", *Optometry & Vision Science*, 1989, vol. 66, No. 8, pp. 518-525.
Balaram, Mini et al., Noncontact Specular Microscopy of Human Lens Epithelium, *IOVS*, vol. 41, No. 2, Feb. 2000, pp. 474-481.
Barak, Adiel et al., "Anterior capsulotomy using the $CO_2$ laser", *Proc. of SPIE*, vol. 3246, 1998, pp. 196-198.
Bath, Patricia E. et al., "Endocapsular Excimer Laser Phakoablation Through a 1-mm Incision", *Opthalmic Laser Therapy*, vol. 2, No. 4, 1987, pp. 245-249.
Beers, A. P. A. et al. "Age-Related Changes in the Accommodation Mechanism", *Optometry and Vision Science*, 1996, vol. 73, No. 4, pp. 235-242.
Beers, A. P. A. et al., "In Vivo Determination of the Biomechanical Properties of the Component Elements of the Accommodation Mechanism", *Vision Res.*, vol. 34, 1994, pp. 2897-2905.
Bellows, John G., M.D. et al., "B. Cataracta Complicata", *Traumatic Cataract*, undated but prior to Jul. 2009, pp. 270-272.
Ben-Sira, I. et al., "Clinical method for measurement of light back scattering from the in vivo human lens", *Invest. Ophthalmol. Vis. Sci.*, vol. 19, No. 4 (Reports), Apr. 1980, pp. 435-437.
Benjamin, William J., "Borish's Clinical Refraction", W.B. Saunders, publishers, copyright 1998, p. 110.
Bettelheim, Frederick A. et al., "Syneretic Response of Aging Normal Human Lens to Pressure", *Investigative Ophthalmology & Visual Science*, vol. 44, No. 1, Jan. 2003, pp. 258-263.
Bigler, Emmanuel, "Depth of field and Scheimpflug's rule: a "minimalist" geometrical approach", published unknown, 2002, pp. 1-17.
Billie, J. F. et al., "3D Imaging of the Human Eye Using the laser Tomographic Scanner Lts", publisher unknown, undated but prior to Jul. 2009, 2 pgs.
Bito, L.Z. et al., "Age-dependent loss of accommodative amplitude in rhesus monkeys: an animal model for presbyopia", *Invest. Ophthalmol. Vis. Sci.*, vol. 23, No. 1, Jul. 1982, pp. 23-31.
Bor, Zs. PhD., et al., "Plume Emission, Shock Wave and Surface Wave Formation During Excimer Laser Ablation of the Cornea". *Supplement to Retroactive & Corneal Surgery*, vol. 9, Mar./Apr. 1993, pp. S111-S115.
Borja, David et al., "Crystalline Lens MTF Measurement During Simulated Accommodation", *Proc. of SPIE*, 2005, vol. 5688, pp. 26-32.
Borkman, Raymond F. et al., "Evidence for a Free Radical Mechanism in Aging and u.v.-Irradiated Ocular Lenses", *Exp. Eye Res.*, 1977, vol. 25, pp. 303-309.

Braham, Lewis, "Eye Surgery: It's Getting Sharper", *Business Week*, Oct. 18, 2004, pp. 142-143.

Breitenfeld, P. et al., "Finite Element Method-Simulation of the Human Lens During Accommodation", publiasher unknown, vol. 5863, 2005, 9 pgs.

Breitling, Detlef et al., "Fundamental aspects in machining of metals with short and ultrashort laser pulses", *Proc. of SPIE*, vol. 5339, 2004, pp. 1-15.

Brian, G. et al., "Cataract Blindness—Challenges for the 21$^{st}$ Century", *Bulletin of the World Health Organization*, vol. 79, No. 3, 2001, pp. 249-256.

Bron, A.J., "The Ageing Lens", *Opthalmologics*, vol. 214, 2000, pp. 86-104.

Brown, Nicholas, "Dating the onset of cataract", *Transactions of the Ophthalmological Society of the United Kingdom*, vol. 96, 1976, pp. 18-23.

Brown, Nicholas "The Change in Lens Curvature with Age", *Exp. Eye Res.* (1974), vol. 19, pp. 175-183.

Brown, Nicholas "The Change in Shape and Internal Form of the Lens of the Eye on Accommodation", *Exp. Eye Res.* (1973) vol. 15, pp. 441-459.

Burd, H.J. et al., "Can reliable values of Young's modulus be deduced from Fisher's (1971) spinning lens measurements?", *Vision Research*, volume unknown, 2005, pp. 1-15.

Burd, H.J. et al., "Numerical modeling of the accommodating lens", *Vision Research*, vol. 42, 2002, pp. 2235-2251.

Campbell, Melanie C. W., "Measurement of Refractive Index in an Intact Crystalline Lens", *Vision Research*, vol. 24, No. 5, 1984, pp. 409-415.

Carey, James et al., "Propagation and Characterization of Ultrashort Laser Pulses", Harvard University, 2003, pp. 1-30.

Charles, M. W. et al., "Dimensions of the Human Eye Relevant to Radiation Protection", *Phys. Med. Biol.*, 1975, vol. 20, No. 2, © 1975, pp. 202-218.

Chen, Wei-Li et al., Ultrasound Biomicroscopic Findings in Rabbit Eyes Undergoing Scleral Suction during Lamellar Refractive Surgery, *IOVS*, vol. 43, No. 12, Dec. 2002, pp. 3665-3672.

Claflin, E. S. et al., "Configuring an electrostatic membrane mirror by least-squares fitting with analytically derived influence functions", *J. Opt. Soc. Am. A.*, vol. 3, No. 11, 1986, pp. 1833-1839.

Coleman, D. Jackson et al., "Presbyopia. Accommodation, and the Mature Catenary", *Ophthalmology*, vol. 108, No. 9, Sep. 2001, pp. 1544-1551.

Cook, Christopher A. et al., "Aging of the Human Crystalline Lens and Anterior Segment", *Vision Res.*, 1994, vol. 34, No. 22, pp. 2945-2954.

Costagliola, Ciro et al., "ArF 193 nm Excimer Laser Corneal Surgery as a Possible Risk Factor in Cataractogenesis", *Exp. Eye Res.*, 1994, vol. 58, pp. 453-457.

Cotlier, Edward, M.D., "The Lens", *Adler's Physiology of the Eye*, copyright 2003, pp. 268-290.

Crawford, Kathryn S. et al., "The Role of the Iris in Accommodation of Rhesus Monkeys", *Investigative Ophthalmology & Visual Science*, vol. 31, No. 10, Oct. 1990, pp. 2185-2190.

Croft, Mary Ann et al., "Accommodation and Presbyopia", publisher unknown, vol. 41, 2001, pp. 33-46.

Croft, Mary Ann et al., "Accommodation and Presbyopia: The Ciliary Neuromuscular View", *Opthalmol Clin N Am*, vol. 19, 2006, pp. 13-24.

Croft, Mary Ann et al., Accommodative Ciliary Body and Lens Function in Rhesus Monkeys, I: Normal Lens, Zonule and Ciliary Process Configuration in the Iridectomized Eye, *IOVS*, vol. 47, No. 3, Mar. 2006, pp. 1076-1086.

Croft, Mary Ann et al., "The Zonula, Lens, and Circumlental Space in the Normal Iridectomized Rhesus Monkey Eye", *IOVS*, vol. 47, No. 3, Mar. 2006, pp. 1087-1095.

Cromie, William J., "Laser Makes History's Fastest Holes", *The Harvard University Gazette*, 1999, obtained at http://www.news.harvard.edu/gazette/1999/10.07/laser.html, 6 pags.

Czygan, G. et al., "Mechanical testing of isolated senile human eye lens nuclei", *Med. Eng. Phys.*, vol. 18, No. 5, 1996, pp. 345-349.

Datta, Debajyoti, "Tissue Surgery and Subcellular Photodisruption with Femtosecond Laser Pulses", *Thesis for Dept. of Physics*, Harvard University, May 2002, pp. 1-74.

Dausinger, Friedrich et al., "Micro-machining with ultrashort laser pulses: From basic understanding to technical applications", publisher unknown, undated but prior to Jul. 2009, pp. 1-10.

Dholakia, Sheena A. et al., "Prospective evaluation of phacoemulsification in adults younger than 50 years", *J Cataract Refract Surg*, vol. 31, 2005, pp. 1327-1333.

Douven, Lucien F.A. et al., "Characterization of Mechanical Behaviour of Human Skin In Vivo", *Proc. of SPIE*, vol. 3914, 2000, pp. 618-629.

Ehrmann, Klaus et al., "Evaluation of porcine crystalline lenses in comparison with molded polymer gel lenses with an improved ex vivo accommodation simulator", *Proc. of SPIE*, vol. 5688, 2005, pp. 240-251.

Ehrmann, Klaus et al., "Ex Vivo Accommodation Simulator II—Concept and Preliminary Results", *Proc. of SPIE*, vol. 5314, 2004, pp. 48-58.

Eisner, Georg, "Eye Surgery—An Introduction to operative technique", Springer-Verlag, Berlin, 1980, pp. 14-19.

El-Osta, Austen A.R. et al., "In vitro model for the study of human posterior capsule opacification", *J Cataract Refract Surg*, vol. 29, 2003, pp. 1593-1600.

Erpelding, Todd N. et al., "Bubble-Based Acoustic Radiation Force for Monitoring Intraocular Lens Elasticity", *IEEE Intl Ultrasonics Symposium*, volume unknown, 2004, pp. 732-735.

Fagerholm, Per P.P., "The Response of the Lens to Trauma", *Trans. Ophtal. Soc. U. K.*, 1982, vol. 102, p. 369-374.

Farnsworth, P.N. et al., "Anterior Zonular Shifts with Age", *Exp. Eye Res.*, vol. 28, 1979, pp. 291-297.

Findl, Oliver et al., "Laserinterferometric Assessment of Pilocarpine-Induced Movement of an Accommodating Intraocular Lens—A Randomized Trial", *Ophthalmology*, vol. 111, No. 8, Aug. 2004, pp. 1515-1521.

Fisher, R.F. et al., "Changes in lens fibres after damage to the lens capsule", publisher unknown, undated but prior to Jul. 2009, 4 pgs.

Fisher, R.F., "Presbyopia and the Changes With Age In The Human Crystalline Lens", *J. Physiol.*, vol. 228, 1973, pp. 765-779.

Fisher, R. F., "The Ciliary Body in Accommodation", *Trans. Opthalmol. Soc. U.K.*, vol. 105, 1986, pp. 208-219.

Fisher, R.F., "The Force of Contraction of the Human Ciliary Muscle During Accommodation", *J. Physiol.*, vol. 270, 1977, pp. 51-74.

Fisher, R. F. et al., "The elastic constants and ultrastructural organization of a basement membrane (lens capsule)", *Proc. R. Soc. Lond. B.*, vol. 193, 1976, pp. 335-358.

Fisher, R.F., "The Elastic Constants of the Human Lens", *J. Physiol.*, vol. 212, 1971, pp. 147-180.

Fisher, R.F., "Elastic Constants of the Human Lens Capsule", *J. Physiol.*, vol. 201, 1969, pp. 1-19.

Fisher, R. F., "The Mechanics of Accommodation in Relation to Presbyopia", *Eye*, vol. 2, 1988, pp. 646-649.

Fleck, Brian W. et al., "Q-switched Nd:YAG laser disruption of rabbit lens nucleus", *Laser and Light in Ophthalmology*, 1990, vol. 3. No. 3, pp. 227-232.

Foster, C. Stephen et al., "Smolin and Thoft's The Cornea: Scientific Foundations and Clinical Practice", *The New England Journal of Medicine*, vol. 353 No. 23, 2005, pp. 2519-2520.

Fujimoto, James et al., "Biomedical Optics", Photonics West, *Proc. of SPIE*, Vol. unknown, 2005, pp. 23-70.

Garner, LF et al., "Changes in Equivalent and Gradient Refractive Index of the Crystalline Lens with Accommodation", *Optom, Vis. Sci.*, vol. 74, No. 2, Feb. 1997, pp. 114-119.

Garner, LF et al., "Changes in Ocular Dimensions and Refraction with Accommodation", *Ophthal. Physiol. Opt.*, vol. 17, No. 1, 1997, pp. 12-17.

Garner, Margaret H. et al., "Selective oxidation of cysteine and methionine in normal and senile cataractous lenses", *Proc. Natl. Acad. Sci. USA*, vol. 77, No. 3, Mar. 1980, pp. 1274-1277.

Gayen, Tapan K. et al., "Near-infrared laser welding of aortic and skin tissues and microscopic investigation of welding efficacy", *Proc. of SPIE*, vol. 4949, 2003, pp. 182-185.

Gershenzon, A. et al., "Clinical and Epidemiology—New software for lens retro-illumination digital image analysis", *Australian and New Zealand Journal of Ophthalmology*, 1999, vol. 27, pp. 170-172.

Giblin, Frank J. et al., "Nuclear Light Scattering, Disulfide Formation and Membrane Damage in Lenses of Older Guinea Pigs Treated with Hyperbaric Oxygen", *Exp. Eye Res.*, 1995, vol. 60, pp. 219-235.

Gills, James P., "Treating astigmatism at the time of cataract surgery", *Current Opinion in Ophthalmology*, 2002, vol. 13, p. 2-6.

Gimbel, Howard V. et al., "Intrastromal Photorefractive Keratectomy with the Nd:YLF Laser", publisher unknown, vol. 34, Iss. 4, 1994, pp. 139-145.

Glasser, Adrian et al., "Accommodative Changes in Lens Diameter in Rhesus Monkeys", *IOVS*, vol. 47, No. 1, Jan. 2006, pp. 278-286.

Glasser, A. et al., "Biometric, optical and physical changes in the isolated human crystalline end with age in relation to presbyopia", *Vision Research*, vol. 39, 1999, pp. 1991-2015.

Glasser, Adrian et al., "On modeling the causes of presbyopia", *Vision Research*, vol. 41, 2001, pp. 3083-3087.

Glasser, A. et al., "On the potential causes of presbyopia", *Vision Research*, vol. 39, 1999, pp. 1267-1272.

Glasser, Adrian et al., "Presbyopia and the Optical Changes in the Human Crystalline Lens with Age", *Vision Res.*, vol. 38, No. 2, 1998, pp. 209-229.

Glasser, Adrian et al., "Ultrasound Biomicroscopy of the Aging Rhesus Monkey Ciliary Region", *Optometry and Vision Science*, vol. 78, No. 6, 2001, pp. 417-424.

Goodenough, Daniel A., "Lens gap junctions: a structural hypothesis for nonregulated low-resistance intercellular pathways", *Invest. Ophthalmol. Visual Sci.*, vol. 18, No. 11, Nov. 1979, pp. 1104-1122.

Grace, Jeffery M. et al., "Repetitively Pulsed Ruby Lasers As Light Sources for High-Speed Photography", *Optical Engineering*, vol. 37, No. 8, Aug. 1998, pp. 1-26.

Gwon, Arlene et al., "Focal laser photophacoablation of normal and cataractous lenses in rabbits: Preliminary report", *J Cataract Refract Surg*, vol. 21, May 1995, pp. 282-286.

Habib, Maged S. et al., "Myopic Intrastromal Photorefractive Keratectomy With the Neodymium-Yttrium Lithium Fluoride Picosecond Laser in the Cat Cornea", *Arch Ophthalmol.*, vol. 113, Apr. 1995, pp. 499-505.

Hahn, D.W., "Dynamics of Ablation Plume Particles Generated During Excimer Laser Corneal Ablation", *Lasers in Surgery and Medicine*, vol. 16, 1995, pp. 384-389.

Hamaoui, Marie et al., "Ex-vivo testing of crystalline lens substitutes: a pilot study", *Proc. of SPIE*, vol. 3908, 2000, pp. 123-130.

Hammer, Daniel X. et al., "Dual OCT/SLO Imager with Three-Dimensional Tracker", *Proc. of SPIE*, vol. 5688, 2005, pp. 33-44.

Hammer, Daniel et al., "Shielding Properties of Laser-Induced Breakdown in Water for Pulse Durations From 5 ns. To 125 fs", *Applied Optics*, 1997, vol. 36, No. 22, pp. 5630-5640.

Hanson, S.R.A. et al., "The major in vivo modifications of the human water-insoluble lens crystallins are disulfide bonds, deamidation, methionine oxidation and backbone cleavage", *Exp. Eye Res.*, vol. 71, 2000, pp. 195-207.

Hara, Tsutomu, M.D. et al., "Complications associated with endocapsular balloon implantation rabbit eyes", *J Cataract Refract Surg*, vol. 20, Sep. 1994, pp. 507 and 512.

Harding, J. J., "Disulphide Cross-linked Protein of High Molecular Weight in Human Cataractous Lens", *Exp. Eye Res.* (1973), vol. 17, pp. 377-383.

Hartwick, Andrew T. E. et al., "Ephitelial activity of hexokinase and glucose-6-phosphate dehydrogenase in cultured bovine lenses recovering from pharmaceutical-induced optical damage", *Molecular Vision*, vol. 9, 2003, pp. 594-600.

Heisterkamp, Alexander et al., "Nonlinear effects inside corneal tissue after fs-photodisruption". *Proc. of SPIE*, vol. 4433, 2001, pp. 55-60.

Heisterkamp, Alexander et al., "Pulse energy dependence of subcellular dissection by femtosecond laser pulses", *Optics Express*, vol. 13, No. 10, May 2005, pp. 3690-3696.

Hemenger, Richard P. et al., "Change With Age of the Refractive Index Gradient of the Human Ocular Lens", *Investigative Ophthalmology & Visual Science*, Mar. 1995. vol. 36, No. 3. pp. 703-707.

Heys, Karl Robert et al., "Massive increase in the stiffness of the human lens nucleus with age: the basis for presbyopia?", *Molecular Vision*, vol. 10, 2004, pp. 956-963.

Ho, A. et al., "Feasibility of simultaneous correction of ametropia by varying gel refractive index with phaco-ersatz", *Proc. of SPIE*, vol. 4245, 2001, pp. 119-128.

Hoffman, Richard S. et al., "Refractive lens exchange as a refractive surgery modality". Copyright © 2004 Lippincott Williams & Wilkins, pp. 22-28.

Holzer, Mike P. et al., "Corneal flap complications in refractive surgery—Part 1: Development of an experimental animal model", *J Cataract Refract Surg*, vol. 29, Apr. 2003, pp. 795-802.

Holzer, Mike P. et al., "Corneal flap complications in refractive surgery—Part 2: Postoperative treatments of diffuse lamellar keratitis in an experimental animal model", *J Cataract Refract Surg*, vol. 29, Apr. 2003, pp. 803-807.

Horwitz, Joseph, "α-Crystallin can function as a molecular chaperone", *Proc. Natl. Acad. Sci. USA*, vol. 89. Nov. 1992, pp. 10449-10453.

Hu, Tian-Shang et al., "Reversal of Galactose Cataract with Sorbinil in Rats", *Investigative Ophthalmology & Visual Science*, May 1983, vol. 24, pp. 640-644.

Huber, G. et al., "Room-temperature 2-μm HO:YAG and 3-μm ER:YAG Lasers", *Journal de Physique*, undated but prior to Jul. 2009, 3 pgs.

Hunter, David, "First, Gather the Data", *New England Journal of Medicine*, vol. 354, No. 4, Jan. 26, 2006, pp. 329-331.

Jacques, Paul F. et al., "Long-term vitamin C supplement use and prevalence of early age-related lens opacities", *Am J Clin Nutr*, 1997; 66, pp. 911-916.

Johannesson, Mattias, "Active Range Imaging 2", PhD-Thesis: SIMD architectures for Range and Radar Imaging, *Linkoping Studies in Science and Technology*, Dissertations No. 399, 2005, pp. 1-34.

Jones, C.E. et al., "Refractive index distribution and optical properties of the isolated human lens measured using magnetic resonance imaging (MRI)", *Vision Research*, vol. 45, 2005, pp. 2352-2366.

Juhasz, Tibor, Ph.D. et al., "Dynamics of Shock Waves and Cavitation Bubbles Generated by Picosecond Laser Pulses in Corneal Tissue and Water", *Lasers in Surgery and Medicine*, vol. 15, 1994, pp. 91-98.

Juhasz, T. et al., "Time resolved observations of shock waves and cavitatin bubbles generated by femtosecond laser pulses in corneal tissue and water", *Lasers in Surgery and Med*, vol. 19, 1996, pp. 23-31.

Juhasz, T. et al., "Time-resolved Studies of Plasma-Mediated Surface Ablation of Soft Biological Tissue with Near-Infrared Picosecond Laser Pulses", *SPIE*, vol. 2975, 1997, pp. 271-281.

* cited by examiner

LASER SYSTEM AND METHOD FOR ASTIGMATIC CORRECTIONS IN ASSOCIATION WITH CATARACT TREATMENT

Applicants claim, under 35 U.S.C. §119(e), the benefit of priority of the filing date of Jul. 24, 2009 of U.S. provisional patent application Ser. No. 61/228,514, filed on the aforementioned date, the entire contents of which are incorporated herein by reference.

BACKGROUND OF THE INVENTION

1. Field of the Invention

The present invention relates to methods and systems for improving procedures that address cataracts, opacifications in the lens, clear lens extraction, removal of natural lens material, use of lens replacement materials and combinations thereof. Specifically, the present invention relates to systems and methods that provide predetermined, precise and reproducible laser shot patterns for creating cuts in the cornea of the eye in predetermined and precise shapes that are reproducible from patient to patient and surgeon to surgeon and which address aberrations in the eye.

2. Discussion of Related Art

The established treatment for cataracts is the removal of the opacified human crystalline lens and its replacement with an intraocular lens ("IOL"). In general, IOLs consist of a small plastic lens with plastic side struts, called haptics, to hold the lens in place within the capsular bag inside the eye. Exemplary types of IOLs include monofocal lenses, multifocal IOLs, which provide the patient with multiple-focused vision at far and reading distance, and accommodative IOLs, which provide the patient with visual accommodation. The flexible nature of many IOLs enables them to be rolled and/or folded up for insertion into the capsule. Examples of IOLs are found in U.S. Pat. Nos. 7,188,949, 6,849,091, 5,699,142 and 5,607,472, the entire disclosures of each of which are incorporated herein by reference. Commercially available IOLs that, by way of example, may benefit from the present invention are CRYSTALENS and ACRYSOF RESTOR.

The CRYSTALENS IOL was developed by Eyeonics and is presently provided by Bausch & Lomb and it is at least in part believed to be disclosed in U.S. Pat. No. 6,849,091. Further information regarding its structure and efficacy is provided by Food and Drug Administration (FDA) PMA P030002 and related documents to that PMA file. The FDA approved indicated use for CRYSTALENS was in part: "The crystalens™ Model AT-45 Accommodating IOL is intended for primary implantation in the capsular bar of the eye for visual correction of apkakia in adult patients in whom a cataractous lens has been removed and is intended to provide near, intermediate, and distance vision without spectacles. The crystalens™ IOL provides approximately one diopter of monocular accommodation." (Nov. 14, 2003 PMA P030002 at Part 2, Summary of Safety and Effectiveness Data, ¶INDICATIONS FOR USE).

Thus, the CRYSTALENS is an example of an FDA approved accommodating IOL. The term "FDA approved accommodating IOL" refers to any IOL that has obtained FDA approval having an indicated use that provides for accommodation, regardless of whether the IOL is actually being employed for such an approved use.

The ACRYSOF RESTOR IOL is provided by Alcon, and it is at least in part believed to be disclosed in U.S. Pat. No. 5,669,142. Further information regarding its structure and efficacy is provided by FDA PMA P040020 and related documents to that PMA file. The FDA approved use for RESTOR was in part: "AcrySOF® ReSTOR® IOLs are indicated for the visual correction of aphakia secondary to removal of a cataractous lens in adult patients with and without presbyopia, who desire near, intermediate and distance vision with increased spectacle independence. The lens is intended to be placed in the capsular bag." (Apr. 24, 2004, PMA P040020, at Part 2, Summary of Safety and Effectiveness Data, ¶INDICATIONS).

Thus, the RESTOR is an example of an FDA approved IOL for near, intermediate and distance vision. The term "FDA approved IOL for near, intermediate and distance vision" refers to any IOL that has obtained FDA approval having an indicated use that provides for near, intermediate and distance vision, regardless of whether the IOL is actually being employed for such an approved use. The CRYSTALENS would also be an example of an FDA approved IOL for near, intermediate and distance vision. Moreover, the RESTOR and CRYSTALENS are examples of an FDA approved IOLs that reduce and/or eliminate the need for spectacles.

The removal of the natural crystalline lens and replacement with a lens replacement material employ the use of a small initial incision or incisions in the limbal area of the eye, which is the transition area between the cornea and sclera. This initial incision is typically made with a small triangular blade that is pushed into the limbal area of the eye. It is through this initial incision that other instruments for use in the removal and replacement of natural lens material are inserted. It is also through this incision that the natural lens material is removed from the eye and replacement lens material is inserted into the eye.

Once the initial incision has been made, the removal of the opacified natural crystalline lens and replacement with a lens replacement material, such as an FDA approved IOL, presently employs a capsulorhexis and/or a capsulotomy. A capsulorhexis generally consists of the removal of a part of the anterior lens capsule and the creation of a hole or opening in the lens capsule, that results from at least in part a tearing action. A capsulotomy generally consists of a cutting of the lens capsule, without or with minimum tearing of the capsule. Thus, to remove the opacified natural lens material, the lens capsule is opened. There are several known techniques for performing a capsulorhexis and a capsulotomy. These would include the technique known as a can opener approach, a Continuous Curvilinear Capsulorhexis (CCC) and the use of a Fugo plasma blade.

SUMMARY

It is desirable to develop systems that would provide greater control in the creation of the incisions and make these improvements patient and surgeon independent, or at least, reduce the variability from patient-to-patient and surgeon-to-surgeon.

The novel and improved methods and systems for the performance of incisions in the cornea in the area of Bowman's membrane, which include aspects of the present inventions and which are set forth in detail in the present patent specification, may provide for better implementation of other methods and systems for delivering laser beams to the lens of the eye, such as those disclosed in published applications US 2007/173794A1, US 2007/173795A1, US 2007/185475A1, WO 2007/084694 A2, and WO 2007/084627A2, the entire disclosures of each of which are incorporated herein by reference.

The present invention, among other things solves this need by providing greater control in the creation of a precise and predetermined incision to the cornea in the area of Bowman's membrane to correct for astigmatism that may be present after replacement of the natural lens of the eye with artificial lens material.

Provided herein are embodiments of the present invention. Thus, there is provided herein a system for providing laser shot patterns to an eye, the system comprising a therapeutic laser that produces a laser beam, a laser shot pattern for performing a capsulotomy, a laser shot pattern for sectioning a lens of an eye and, a laser shot pattern for proving a sub-Bowman's membrane arcuate cut in the cornea. Thus, the laser system is capable of providing the arcuate cut in a manner that does not disrupt Bowman's membrane and reduces astigmatism. These arcuate patterns may be oriented along the steep axis, have about a 3 mm radius, have an arc of about 60°, of about 90° and from about 60° to about 90°. Further the system may have an arcuate pattern that has an arc of about less than 90° and about greater than or equal to 60°, an arcuate pattern has about a 3 mm radius and an arc of about 90° to about 60°.

There is also provided a system for reducing astigmatism associated with replacement of a natural human lens with a lens replacement material, the system including: a laser for providing a laser beam; a controller having associated with it a shot pattern; the shot pattern having two arcuate patterns oriented on the eye along the steep axis; and, the system capable of delivering the laser beam in the shot pattern below Bowman's membrane to treat astigmatism.

There is further provided a system having a therapeutic laser for producing a laser beam, a laser shot pattern for proving a pair of arcuate cuts in the cornea, the shot pattern having a depth of about less than or equal to the thickness of the cornea. The system is thus capable of providing the arcuate cuts in a manner that do not disrupt the epithelium of the eye and reduces astigmatism.

There is yet further provided arcuate patterns of these systems wherein the arcuate pattern is oriented along the steep axis, the arcuate pattern has about a 3 mm radius, the arcuate pattern has an arc of about 60°, the arcuate pattern has an arc of about 90°, and the arcuate pattern has an arc of about less than 90° and about greater than or equal to 60°.

There is additionally provided a method for performing cataract surgery and reducing residual astigmatism by using a laser system including: first, positioning an eye of a patient with respect to the laser system; second, directing the laser system to perform a capsulotomy on the eye; and, third, directing the laser system to deliver a pair of arcuate laser shot patterns to the cornea of the eye, thereby reducing astigmatism while not disrupting the epithelium.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

In general, the present inventions relate to methods and systems for providing a laser to the cornea of the eye to address, improve and correct aberrations of the eye. In particular, the present inventions relate to methods and systems for addressing aberrations of the eye that are present prior to and after the natural human crystalline lens has been removed and replaced with a lens replacement material, and in particular to address astigmatism.

The present methods and systems can be used with the novel and innovative laser system techniques that are the subject of the co-pending patent applications that are cited herein and which have been incorporated herein by reference, and the present methods and systems may possibly be used with other laser delivery systems for the removal of lens material to the extent such systems may be developed in the future. Preferably, the present methods and systems can be incorporated into and used in conjunction with the systems of the co-pending applications that have been incorporated herein by reference. In this way a single system, with a single therapeutic laser, can perform the cuts necessary to remove and replace the natural lens and correct any remaining aberrations.

Novel and pioneering laser systems and methods for the removal and replace of lens material are disclosed in regular and provisional U.S. patent application Ser. No. 61/228,506, Ser. No. 61/228,529, Ser. No. 61/228,484, Ser. No. 12/509,412, and Ser. No. 12/509,211, wherein the entire disclosures of each of which are incorporated herein by reference.

Thus, in general, the present invention provides for a laser system, i.e., a laser device for delivering a laser to the cornea of the eye. In general the laser system has a treatment or therapeutic laser, optics for delivering the laser beam from the treatment laser to the eye, and a particular pattern which provides for the placement of treatment laser shots in the cornea to create arcuate area of tissue removal, i.e., cuts, below the surface of the cornea and in the general area of Bowman's membrane.

Figure 1:
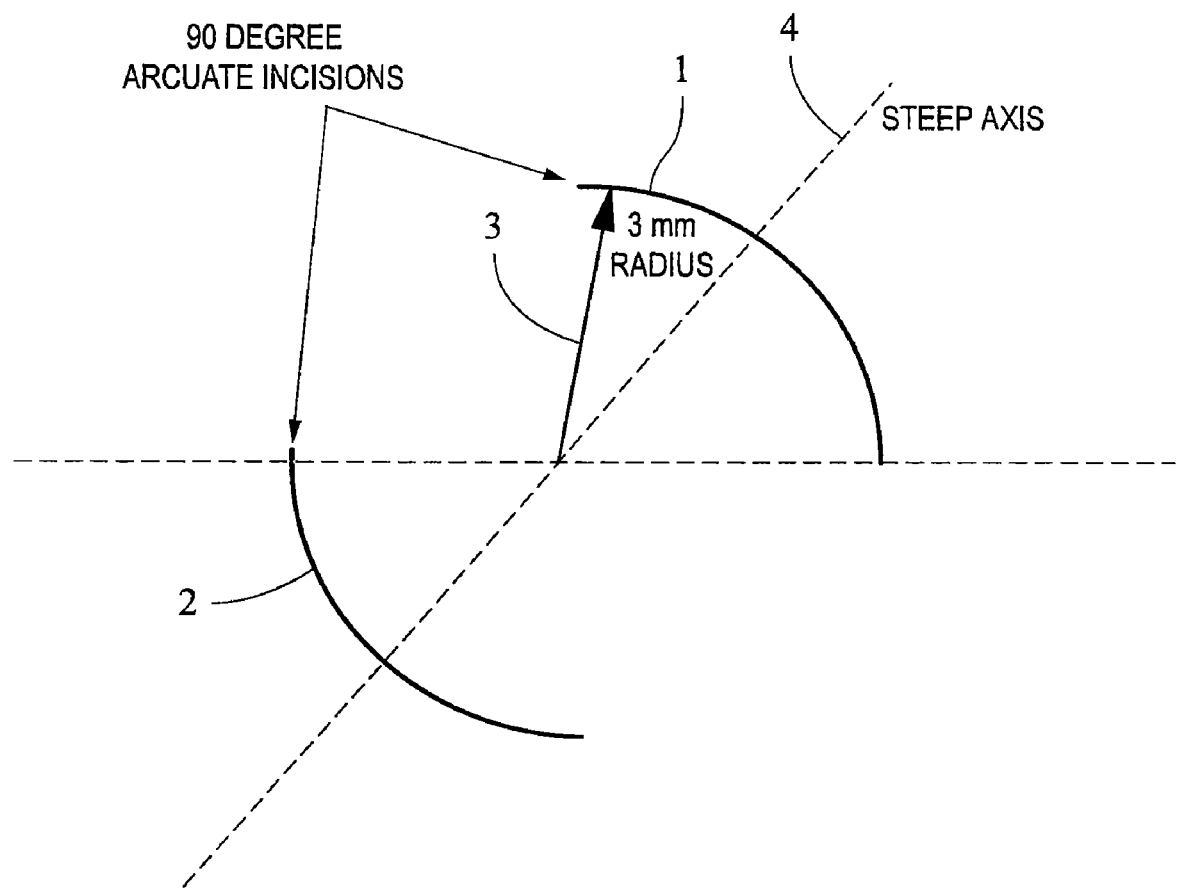
FIG. 1 is a schematic diagram of an embodiment of arcuate patterns in accordance with the present invention.

Referring now to FIG. 1 there is provided an example of a clear corneal incision (CCI) in an arcuate pattern and resultant arcuate cuts of the present invention. Thus, there is provided a first arcuate cut pattern 1 and a second arcuate cut pattern 2. These arcuate cut patterns have a 3 mm radius, shown by arrow 3, and have an arc of 90°. The cut patterns 1 and 2 are oriented along the steep axis 4. Note that one of ordinary skill in the art of correction of astigmatism would readily understand that the steep axis 4 regards an axis of curvature of the cornea that is steeper in curvature than another axis of curvature of the cornea. In this example the patterns and resultant cuts are entirely below Bowman's membrane and in this manner they are made without cutting through or disrupting the epithelium and without cutting through or disrupting Bowman's membrane. The pattern and resultant cut have a depth or thickness that is approximately 90% of the remaining thickness of the cornea.

Further embodiments and variations of this example would include arc patterns less than 90° and greater than and including 60° degrees. It is presently believed that the 90° arc pattern is an appropriate treatment of −4 to −6 cylinder diopters of astigmatism and the 60° arc pattern is an appropriate treatment for −2 to −3.5 cylinder diopters. The depth of the cuts can be from about 90% of the thickness of the cornea to about 60% of the thickness of the cornea, and from about 518 μm to about 400 μm. Although it is preferred that the cuts be below Bowman's membrane, and thus not disturb that membrane and the structures anterior to it, it is contemplated that the cuts may be made slightly above, at or starting on, or slightly below that membrane. The radius of the CCI can range from about 2.6 to 3.2 mm and preferably are about 3 mm. The amount of astigmatic correction is dependent upon the radius of the CCI.

Employment of the CCIs of the present invention can be to correct astigmatism that is present prior to any cataract treatment, that is caused in whole or in part by a cataract treatment, and that is residual after a cataract treatment, whether caused by the treatment or not.

Figure 2:
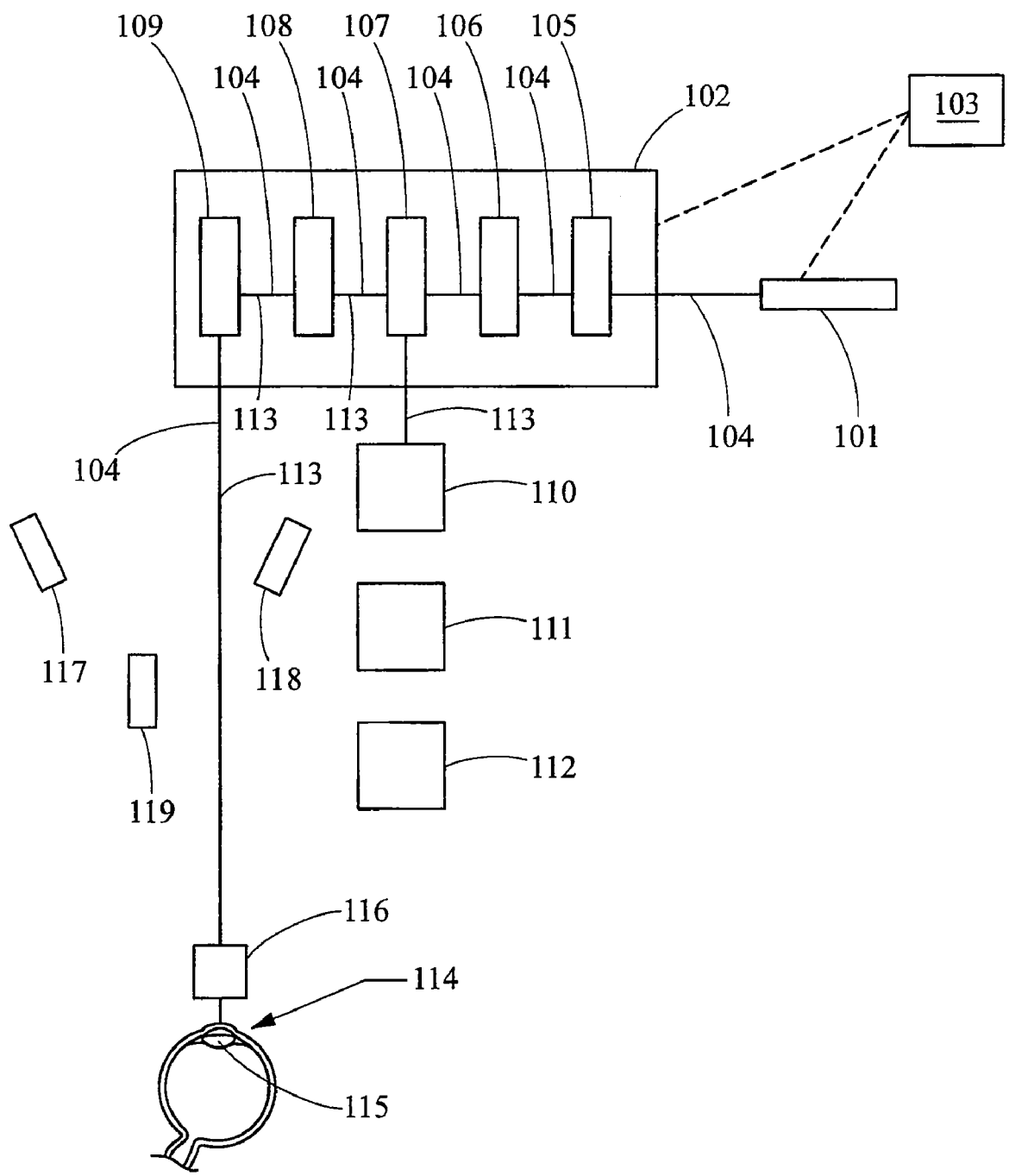
FIG. 2 is a schematic diagram of an embodiment of a system in accordance with the present invention for delivering the arcuate patterns of FIG. 1.

Thus, in general a preferred laser system, i.e., a laser device, for treating patients is provided as shown by way of example in FIG. 2. In this system there is provided a treatment laser 101; optics 102 for delivering the laser beam 104; a control system 103 for delivering the laser beam to the lens in a particular pattern, which control system 103 is associated with and/or interfaces with the other components of the system, as shown for example by dashed lines in FIG. 2, and/or other control systems not shown in FIG. 2.

In general, a laser system for providing the arcuate pattern and creating the resultant arcuate cuts in the cornea has by way of example and referring to FIG. 2, a treatment laser 101 which should provide a beam 104. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. The term photodisruption has also been generally referred to as Laser Induced Optical Breakdown (LIOB). In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in U.S. Patent Application Publication No. 2007/084694 A2 and WO 2007/084627A2, the entire contents of each of which are incorporated herein by reference. These and other similar lasers may be used as therapeutic lasers. For procedures on the cornea the same type of therapeutic laser as described herein may be used, with the energy and focal point being selected to perform the desired procedure.

In general, the optics 102 for delivering the laser beam 104 to the structures of the eye should be capable of providing a series of shots to the natural lens in a precise and predetermined pattern in the x, y and z dimension. The z dimension as used herein refers to that dimension which has an axis that corresponds to, or is essentially parallel with the A-P axis of the eye. The optics should also provide a predetermined beam spot size to cause photodisruption with the laser energy reaching the structure of the eye intended to be cut.

In general, the control system 103 for delivering the laser beam 104 may be any computer, controller, and/or software hardware combination that is capable of selecting and controlling x-y-z scanning parameters and laser firing. These components may typically be associated at least in part with circuit boards that interface to the x-y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser and/or from a separate controller for the slit scanned laser system.

The laser optics 102 for delivering the laser beam 104 includes a beam expander telescope 105, a z focus mechanism 106, a beam combiner 107, an x-y scanner 108, and focusing optics 109. There is further provided relay optics 110, camera optics 111, which include a zoom, and a first ccd camera 112.

Optical images of the eye 114 and in particular optical images of the natural lens 115 of the eye 114 are conveyed along a path 113. This path 113 follows the same path as the laser beam 104 from the natural lens 115 through the laser patient interface 116, the focusing optics 109, the x-y scanner 108 and the beam combiner 107. There is further provided a laser patient interface 116, a structured light source 117 and a structured light camera 118, including a lens. Examples of patient interface and related apparatus that are useful with the present system are provided in regular and provisional U.S. patent application Ser. No. 12/509,021 and Ser. No. 61/228,457, wherein the disclosures of each of which are incorporated herein by reference.

The structured light source 117 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5, which is also referred to as a slit scanned laser. In this embodiment the structured illumination source 117 also includes slit scanning means 119.

When using a scanned slit illumination, the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

The structured light illumination source 117 and the structured light camera 118 are arranged in an angled relationship. The angled relationship may be but is not required to be in the so-called Scheimpflug configuration, which is well-known. The structured light source 117, in conjunction with the slit scanning means 119, projects a line and or a plurality of lines onto the eye lens 115 at an angle or plurality of angles. The light scattered at the eye lens 115 forms the object to be imaged by the lens and focused onto the camera system 118. Since the slit illuminated image in the eye lens 115 may be at a large angle with respect to the camera 118, this presents a large depth of field to the camera and the entire slit image may not be in sharp focus at the camera. By tilting the camera at an angle or plurality of angles the image along the illuminated plane can be in sharper focus. To the extent that a shaped focus is not obtained, arithmetic data evaluation means are further provided herein to determine a more precise location of the illuminated structures with respect to the laser device.

The images from the camera 118 may be conveyed to the controller 103 for processing and further use in the operation of the system. They may also be sent to a separate processor and/or controller, which in turn communicates with the controller 103. The structured light source 117, the camera 118 and the slit scanning means 119 includes a means for determining the position and apex of the lens in relation to the laser system.

The delivery of laser shot patterns and cuts per FIG. 1 for the removal of lens material is provided. Thus, there are provided methods and systems for producing cuts, i.e., incisions in the anterior lens capsule. These cuts are created by the therapeutic laser beam 104 being delivered to the anterior lens capsule in precise predetermined and highly reproducible patterns, delivery results in precise, predetermined, and highly reproducible shaped cuts in patterns as described and taught herein, or as may be called for by the use of a particular IOL or other device or material to be inserted within the lens capsule. As used herein geometric shaped patterns or cuts referrer to circular and elliptical shaped patterns or cuts. As used herein non-geometric shaped patterns or cuts refers to all other shapes that are not circular or elliptical.

The methods and systems to create these cuts in the anterior capsule provide superior results to the handheld methods and apparatus previously known for performing capsulorhexis and capsulotomy, and thus, the methods and systems disclosed herein are considered to be a substantial advancement in these techniques. In addition the delivery of the laser beam shots in a manner that greatly reduces the risk of a missed cut, which depending upon the particular application may be very significant is provided. Moreover, as provided in the following examples, anterior capsule cuts are envisioned and provided that may be a continuous cuts, cuts and lands (uncut capsule portions between cuts) and perforations. Thus, as used herein the terms "missed cut" or "missed cuts" refer to a cut that was intended to be carried out by the delivery of a particular laser shot pattern, but which did not occur because the laser beam missed the lens capsule or targeted lens material. Thus, in a cut and land pattern the lands would not be considered missed cuts, if they were intended to be left uncut by the laser pattern.

The cuts in the lens anterior surface are for the purpose of creating an opening in the lens capsule for the remove of the interior structures of the lens. To facilitate this removal there are provided various laser shot patterns that cut the interior structure of the lens into small volumes, which volumes can then be removed from the lens capsule. These small volumes can range from about 1 mm$^2$ to about 16 mm$^2$ and more preferably from about 2.5 mm$^2$ to about 4 mm$^2$. Thus, a grid laser shot pattern within the interior structures of the lens, which creates cube shaped volumes of interior lens material, can be employed. These cubes can range in size from a side having a length of about 100 μm to about 4 mm, with about 500 μm to 2 mm being a preferred size. Additionally, this invention is not limited to the formation of cubes and other volumetric shapes of similar general size may be employed. For example, arrangement of other shapes such as triangles and pie sliced volumes may be employed.

The laser cut in the anterior capsule is used to create a small opening in the lens anterior surface of the lens capsule for removal of the sectioned volumes of interior material. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the opening is variable and precisely controlled and preferably for presently known lens refilling materials and IOLs is 2 mm or less diameter for lens refilling applications and about 5 mm for IOLs.

The order in which these activities are performed may depend upon the particular characteristics of the internal lens structure, the density of the cataract, the position of the cataract, the type of device used to remove the internal lens material once it has been sectioned into small volumes, the type and power of the laser used, the amount and size of gas bubbles that are produced by the laser, and other factors. Thus, although the examples herein provide for an order of performing the activity of cutting the anterior surface of the lens and sectioning the interior structures of the lens, it should be recognized that this order can be changed, as well as, performed essentially simultaneously or simultaneously.

The preferred laser system for treating patients is capable of making precise and predetermined cuts in the capsule of the lens thus giving rise to capsulotomies that are of precise and predetermined shapes. Thus, there is provided the method of obtaining and analyzing the shape and structure of an IOL, and in particular obtaining and analyzing the shape and structure of an accommodating IOL, an IOL that reduces and/or eliminates the need for spectacles, and/or an IOL for near, intermediate and distance vision, including but limited to FDA approved versions of said IOLs. Based upon this analysis an optimized shape and position for the capsulotomy for use with a particular IOL, or grouping of similarly shaped IOLs, is determined. A predetermined shot pattern for making this optimized shaped capsulotomy is then provided to the laser system, preferably by providing the shot pattern to the control system 103. The laser system can then be used for any one or all of the following procedures, determining the shape and position of the anterior surface of the lens, and in particular the anterior surface of the lens capsule, determining the apex of the lens capsule in relation to the laser system, performing a laser capsulotomy having the precise and predetermined shape selected for a particular type of IOL, and removal of the natural lens material.

Thus, there is provided techniques, systems and apparatus to deliver a laser beam in a shot pattern to the lens of the eye and in particular to the capsule of the lens of the eye in a precise and predetermined manner to provided for a precise predetermined capsulotomy. The shape of these patterns may be delivered using either the jigsaw or ring delivery sequences.

There is further provided herein the use of laser shot patterns having a large range of Z swept at a high rate of speed, while the X-Y position is moved in a circular, or elliptical or other pattern or desired shape, more slowly so that the laser cutting action occurs multiple times over essentially the same X-Y position. Thus, it could be envisioned that the laser beam is operating like the tip of a jigsaw blade moving up and down rapidly compared to the X-Y positioning to create the cut shape. In this way, if the anterior capsule shifts during the cut, due to gas bubble propagation or any other reason, the cut will still be made to the capsule, albeit perhaps outside the center region of the z direction up-down distribution of shots, and more to the anterior or posterior ends of that distribution. For laser cutting of the nucleus where a great deal of bubble buildup is created, a Z range, or up-down range of the cut should be approximately 1 mm in extent, nominally centered on the anterior capsule which would allow approximately +/−475 μm of capsule movement and still provide cutting of a 25 μm thick capsule.

In addition to enabling cutting of a capsule that moves during the procedure, this procedure can be used to compensate for static errors in capsule position due to for example measurement errors. In this way the extent of the Z range may be increased by the known error of the system.

In addition to the large Z range sweeps disclosed herein, there is also contemplated the use of a smaller Z range of cut motion for the case where the uncertainty in capsule position from both static measurement error and anticipated change in position might be smaller, perhaps in the range of hundreds of μm or in the case of highly precise measurement data and near zero movement of the capsule during surgery. In such a case the Z range could be tens of μm—enough range to cut through the capsule thickness.

Further methods and systems to define a high accuracy position measurement of structures of the eye and in particular the anterior capsule, so as to provide in general greater accuracy, precisions and reproducibility from patient to patient for procedures on the eye and in particular capsulotomies, is provided in regular U.S. patent application Ser. No. 12/509,412, the entire disclosure of which is incorporated herein by reference.

In the laser shot patterns provided herein it is preferred that the placement of individual shots with respect to adjacent shots in the pattern are sufficiently close enough to each other, such that when the pattern is complete a sufficiently continuous layer and/or line and/or volume of material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock wave propagation, and gas bubble expansion and contraction. Thus, the timing of sequential pulses such that they are timed faster than some of, elements of, or all of those effects, can increase volumetric removal and/or cleaving efficiency. Accordingly, it is proposed to use pulse repetition frequencies from 50 MHz to 5 GHz, which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption. The terms first, second, third, etc. as used herein are relative terms and must be viewed in the context in which they are used. They do not relate to timing, unless specifically referred to as such.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A system for providing laser shot patterns to an eye, the system comprising:
    a therapeutic laser for producing a laser beam;
    optics for receiving the laser beam and directing the laser beam to an eye so that: 1) a laser shot pattern for performing a capsulotomy is generated, 2) a laser shot pattern for sectioning a lens of an eye is generated; and 3) a laser shot pattern for providing a sub-Bowman's membrane arcuate cut in a cornea of the eye, wherein the laser system provides the sub-Bowman's membrane arcuate cut in a manner that does not disrupt Bowman's membrane of the eye and reduces astigmatism of the eye; and
    wherein the sub-Bowman's membrane arcuate pattern is oriented along a steep axis so as to be intersected by the steep axis.

2. The system of claim 1 wherein the sub-Bowman's membrane arcuate pattern has about a 3 mm radius.

3. The system of claim 1 wherein the sub-Bowman's membrane arcuate pattern has an arc of about 60°.

4. The system of claim 1 wherein the sub-Bowman's membrane arcuate pattern has an arc of about 90°.

5. The system of claim 1 wherein the sub-Bowman's membrane arcuate pattern has an arc of about less than 90° and about greater than or equal to 60°.

6. The system of claim 1 wherein the sub-Bowman's membrane arcuate pattern has about a 3 mm radius and an arc of about 90° to about 60°.

7. A system for reducing astigmatism associated with replacement of a natural human lens with a lens replacement material, the system comprising:
    a laser for providing a laser beam;
    a controller in communication with the laser and controlling the laser beam so as that a shot pattern is generated on an eye, wherein the shot pattern comprises two arcuate patterns oriented on the eye along a steep axis so as to be intersected by the steep axis, wherein the system delivers the laser beam generating the shot pattern below Bowman's membrane of the eye to treat astigmatism of the eye.

8. The system of claim 7 wherein each of the pair of arcuate patterns has about a 3 mm radius.

9. The system of claim 7 wherein each of the pair of arcuate patterns has an arc of about 60°.

10. The system of claim 7 wherein each of the pair of arcuate patterns has an arc of about 90°.

11. The system of claim 7 wherein each of the arcuate patterns has an arc of about less than 90° and about greater than or equal to 60°.

12. The system of claim 7 wherein each of the pair of arcuate patterns has about a 3 mm radius and an arc of about 90° to about 60°.

13. The system of claim 7 wherein each of the pair of arcuate patterns has a depth of about less than or equal to a thickness of the cornea of the eye.

14. A system for providing an arcuate shot pattern to an eye, the system comprising:
    a therapeutic laser for producing a laser beam;
    optics for receiving the laser beam and directing the laser beam to an eye so that an arcuate shot pattern having a depth of about less than or equal to a thickness of a cornea of the eye is generated, wherein the laser system provides the arcuate shot pattern in a manner that does not disrupt an epithelium of the eye and reduces astigmatism of the eye; and
    wherein the arcuate shot pattern is oriented along a steep axis so as to be intersected by the steep axis.

15. The system of claim 14 wherein the arcuate shot pattern has about a 3 mm radius.

16. The system of claim 14 wherein the arcuate shot pattern has an arc of about 60°.

17. The system of claim 14 wherein the arcuate shot pattern has an arc of about 90°.

18. The system of claim 14 wherein the arcuate shot pattern has an arc of about less than 90° and about greater than or equal to 60°.

19. A method for performing cataract surgery and reducing residual astigmatism by using a laser system comprising:
positioning an eye of a patient with respect to a laser system;
directing the laser system to perform a capsulotomy on the positioned eye;
directing the laser system to deliver a pair of arcuate laser shot patterns to a cornea of the eye, wherein each of the pair of arcuate laser shot patterns is oriented along a steep axis so as to be intersected by the steep axis, thereby reducing astigmatism of the eye while not disrupting an epithelium of the eye.

20. The method of claim 19 wherein each of the pair of arcuate laser shot patterns has about a 3 mm radius.

21. The method of claim 19 wherein the arcuate laser shot pattern has an arc of about 60°.

22. The method of claim 19 wherein the arcuate laser shot pattern has an arc of about 90°.

23. The method of claim 19 wherein the arcuate laser shot pattern has an arc of about less than 90° and about greater than or equal to 60°.

24. The method of claim 19 wherein the arcuate laser shot pattern has about a 3 mm radius and an arc of about 90° to about 60°.

25. The method of claim 19 wherein the arcuate laser shot pattern has a depth of about less than or equal to a thickness of the cornea of the eye.

* * * * *

(12) EX PARTE REEXAMINATION CERTIFICATE (21st)

Ex Parte Reexamination Ordered under 35 U.S.C. 257

United States Patent
Naranjo-Tackman et al.

(10) Number: US 8,382,745 C1
(45) Certificate Issued: Jan. 29, 2015

(54) LASER SYSTEM AND METHOD FOR ASTIGMATIC CORRECTIONS IN ASSOCIATION WITH CATARACT TREATMENT

(75) Inventors: Ramón Naranjo-Tackman, Mexico City (MX); Jorge Octavio Villar Kuri, Mexico City (MX); Rudolph W. Frey, Maitland, FL (US)

(73) Assignee: PDL Biopharma, Inc., Incline Village, NV (US)

Supplemental Examination Request:
No. 96/000,047, Dec. 3, 2013

Reexamination Certificate for:
Patent No.: 8,382,745
Issued: Feb. 26, 2013
Appl. No.: 12/831,845
Filed: Jul. 7, 2010

Related U.S. Application Data

(60) Provisional application No. 61/228,514, filed on Jul. 24, 2009.

(51) Int. Cl.
*A61B 18/18* (2006.01)

(52) U.S. Cl.
USPC ..................................... 606/5; 606/10; 606/4

(58) Field of Classification Search
None
See application file for complete search history.

(56) References Cited

To view the complete listing of prior art documents cited during the supplemental examination proceeding and the resulting reexamination proceeding for Control Number 96/000,047, please refer to the USPTO's public Patent Application Information Retrieval (PAIR) system under the Display References tab.

*Primary Examiner* — Deandra Hughes

(57) ABSTRACT

There is provided a system, apparatus and methods for developing laser systems that can create precise predetermined clear corneal incisions that are capable of reducing astigmatism. The systems, apparatus and methods further provide laser systems that can provide these incisions at or below Bowman's membrane and in conjunction a precise predetermined capsulotomy shot pattern.

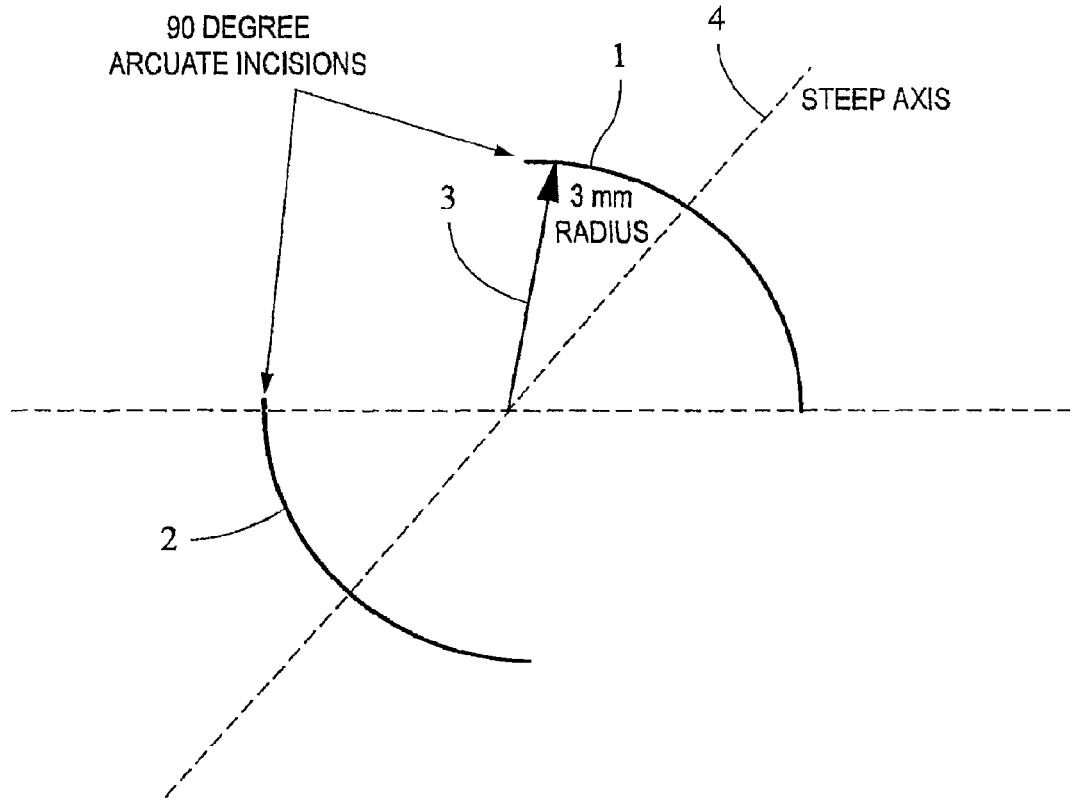

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-25 is confirmed.

\* \* \* \* \*